(12) United States Patent
Haveri

(10) Patent No.: US 7,081,745 B2
(45) Date of Patent: Jul. 25, 2006

(54) PARAMAGNETIC OXYGEN SENSING APPARATUS AND METHOD

(75) Inventor: Heikki Haveri, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 83 days.

(21) Appl. No.: 10/511,068

(22) PCT Filed: Mar. 14, 2003

(86) PCT No.: PCT/IB03/01052

§ 371 (c)(1),
(2), (4) Date: Oct. 12, 2004

(87) PCT Pub. No.: WO03/081225

PCT Pub. Date: Oct. 2, 2003

(65) Prior Publication Data

US 2005/0212507 A1    Sep. 29, 2005

Related U.S. Application Data

(60) Provisional application No. 60/366,876, filed on Mar. 22, 2002.

(51) Int. Cl.
*G01R 33/16* (2006.01)
*G01R 33/12* (2006.01)

(52) U.S. Cl. .................. 324/204; 73/24.01; 73/24.05; 73/30.02

(58) Field of Classification Search .............. 324/204
See application file for complete search history.

(56) References Cited

U.S. PATENT DOCUMENTS

| 3,049,665 A | 8/1962 | Hummel |
| 3,347,087 A | 10/1967 | Engelhardt et al. |
| 3,487,297 A | 12/1969 | Guyton |
| 3,584,499 A | 6/1971 | Hummel |
| 4,633,705 A | 1/1987 | Merilianen et al. |
| 4,683,426 A | 7/1987 | Hummel |

FOREIGN PATENT DOCUMENTS

| DE | 29 00 624 | 7/1979 |
| DE | 35 05 490 | 8/1986 |
| FR | 2668264 | 4/1992 |

OTHER PUBLICATIONS

Patent Abstracts of Japan, vol. 1997, No. 07, Jul. 31, 1997 & JP 09 072803 (Tokyo Gas Col. Ltd.) Mar. 18, 1997 Abstract.

*Primary Examiner*—Bot LeDynh
(74) *Attorney, Agent, or Firm*—Andrus, Sceales, Starke & Sawall, LLP

(57) ABSTRACT

A paramagnetic oxygen sensor and method employs a pressure sensor having a membrane extending through an air gap for a magnetic field. A piezoelectric element is mounted on the membrane. Gas chambers are formed on either side of the membrane. The gas mixture, the properties of which are to be measured, is supplied to one of the chambers. A reference gas is applied to the other chamber. A pulsating magnetic field is provided across the air gap and through the chambers containing the gas mixture and reference gas. The differing responses of the gas mixture and reference gas to the magnetic field deflect the membrane. The deflection of the membrane is sensed by the piezoelectric element. The piezoelectric element maybe operated either in a passive mode or active mode to sense the deflection of the membrane.

40 Claims, 10 Drawing Sheets

PRIOR ART

PARAMAGNETIC OXYGEN SENSING APPARATUS AND METHOD

CROSS REFERENCE TO RELATED APPLICATION

The present application is the U.S. national stage application of International Application PCT/IB03/01052, filed Mar. 14, 2003, which international application was published on Oct. 2, 2003 as International Publication WO 03/081225. The International Application claims priority of U.S. Provisional Application No. 60/366,876, filed Mar. 22, 2002.

BACKGROUND OF THE INVENTION

A paramagnetic oxygen sensor employs the following principles. An atom consists of a nucleus that is surrounded by orbiting electrons. An orbit can be occupied by up to two electrons, and one or more orbits make up an electron shell. In addition, each electron spins around its own axis and has a magnetic moment associated with the electron spin. The magnetic properties of the whole atom are then determined by the combined effect of the spins of all the electrons. Two paired electrons in the same orbit have opposite spins, which cancel their magnetic effects. However, oxygen is one of the rare molecules that has unpaired orbiting electrons around the nucleus and thus a magnetic property. It has an even number of electrons orbiting around the nucleus, but two of them are in unpaired orbits. This makes the oxygen molecule strongly susceptible to interaction with an external magnetic field.

The strength of the interaction between a molecule and a magnetic field is called magnetic susceptibility. Substances having positive magnetic susceptibility are called paramagnetic and those with negative susceptibility, diamagnetic. Positive susceptibility means that a molecule is attracted by a magnetic field, negative susceptibility means that it is repelled by it. Oxygen is the only gas that is paramagnetic, whereas other gases are weakly diamagnetic. This physical phenomenon offers a specific way to measure the oxygen content of a respiratory gas mixture, even when nitrous oxide is present.

In 1968 H. Hummel presented a way of using the paramagnetic principle by constructing a cell in which two gases were mixed inside a homogenous magnetic field. By using an alternating magnetic field, it is possible to measure a difference in pressure between the gases in two conduits upstream of the cell. The amplitude of this signal is directly proportional to the difference in oxygen partial pressure between the two gases to be measured. See U.S. Pat. No. 3,584,499. When the active volume of the measuring cell is made very small, the response time is fast enough for breath-by-breath measurements. The cell was commercialized, but it was bulky in size and sensitive to external vibrations and pressure.

The Datex Division of the Instrumentarium Corporation studied and further developed the Hummel cell configuration into a compact, fast, differential cell for measuring oxygen consumption. This oxygen analyzer is described in U.S. Pat. No. 4,633,705. The analyzer, which basic configuration is shown in FIG. 1, is constructed of an electromagnet with a thin air gap ensuring an essentially constant magnetic field between its poles. The gas to be measured and a reference gas are conducted to this air gap where they are mixed in the uniform magnetic field and then the mixture is conducted out from the gap. A reference gas is needed to measure the absolute oxygen fraction of the measured gas. A pressure difference proportional to the content of oxygen in the gas exists inside the three conduits entering the gap with a fixed magnetic field. If the oxygen content in the two gases differs, a pressure difference will exist between the inlet conduits outside the gap when the magnetic field is on. By selecting a proper switching frequency, the generated pressure signal can be detected by a differential pressure transducer connected between the inlet conduits. Although this oxygen analyzer is very compact, fast, and accurate it still has a few disadvantages.

The pressure signal is not measured in the exact spot where it is generated. The signal is transferred to the differential pressure sensor via tubing, connectors and additional volume, which moderate the signal amplitude. The associated pressure transfer function also depends on the properties of the gas and results in asymmetry between the two branches of the differential pressure sensor. Interfering mechanical background signals cause common-mode error, the magnitude of which is affected by the pressure sensor and gas composition. Some errors are introduced when the velocity of the gas changes, as occurs with changes either of the pump power or gas viscosity. The end of the reference tubing is usually under ambient pressure, but the sampling tubing is connected to a breathing circuit. The external pressure disturbance, the overpressure generated by the ventilator, is transmitted into cell and is detected by the pressure sensor. Another type of disadvantage is the continuous need of reference gas flow, which is a disadvantage in closed-circuit anesthesia when room air cannot be used as a reference, because it would result in a slow accumulation of nitrogen in the breathing circuit.

SUMMARY OF THE PRESENT INVENTION

This invention also utilizes the magnetic susceptibility of oxygen molecules for measuring the oxygen content of a respiratory gas mixture. The pressure difference $\Delta p$ of oxygen content is measured in the exact spot where it is generated, inside the air gap of an electromagnetic circuit. The magnetic field is switched on and off cyclically. A thin, disk shaped pressure sensor, which is used to measure the partial pressure of oxygen, is located between the magnet poles in the middle of the air gap.

The functioning of the pressure sensor is based on piezoelectricity, since piezoelectric crystals can convert mechanical energy to electrical energy with a good efficiency. Piezoelectric crystals can sense pressures directed to them both passively and actively. In passive sensing the piezoelectric crystal converts the pressure change applied to it into an electrical voltage spike between its electrodes. The amplitude of voltage is proportional to intensity of the applied pressure. Thus in passive sensing, piezoelectric crystal is sensitive for alternating pressure, but insensitive for static pressure. In active sensing the piezoelectric crystal is excited to a mechanical vibration near or at the mechanical resonant frequency of the piezoelectric sensor by applying an alternating electrical voltage to its electrodes. Pressure directed to the vibrating sensor functions as a mechanical load for the piezoelectric crystal and can be measured as a change in the electrical properties of the piezoelectric sensor. Active sensing consumes energy but it is 10–100 times more sensitive than passive sensing, depending on the Q-value of the transducer.

BRIEF DESCRIPTION OF THE DRAWING

FIGS. 2a and 2b show an embodiment of the oxygen sensor of the present invention, FIG. 2b being a cross-sectional view taken along the line A—A of FIG. 2a.

FIGS. 11a and 11b show another embodiment of the oxygen sensor of the present invention, FIG. 11b being a cross-sectional view taken along the line of A—A of FIG. 11a.

DETAILED DESCRIPTION OF THE PRESENT INVENTION

Figure 1:
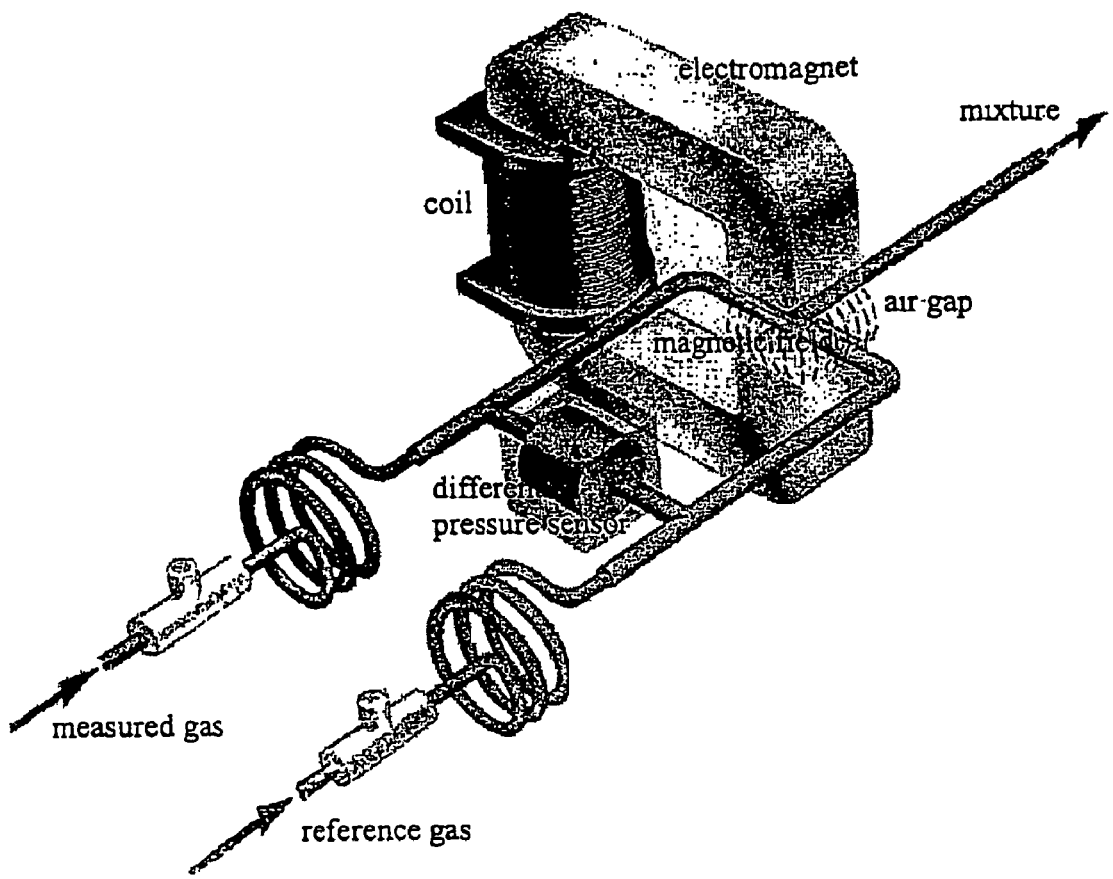
FIG. 1 is a view showing a prior art paramagnetic oxygen sensor.
Figures 2A, 2B:
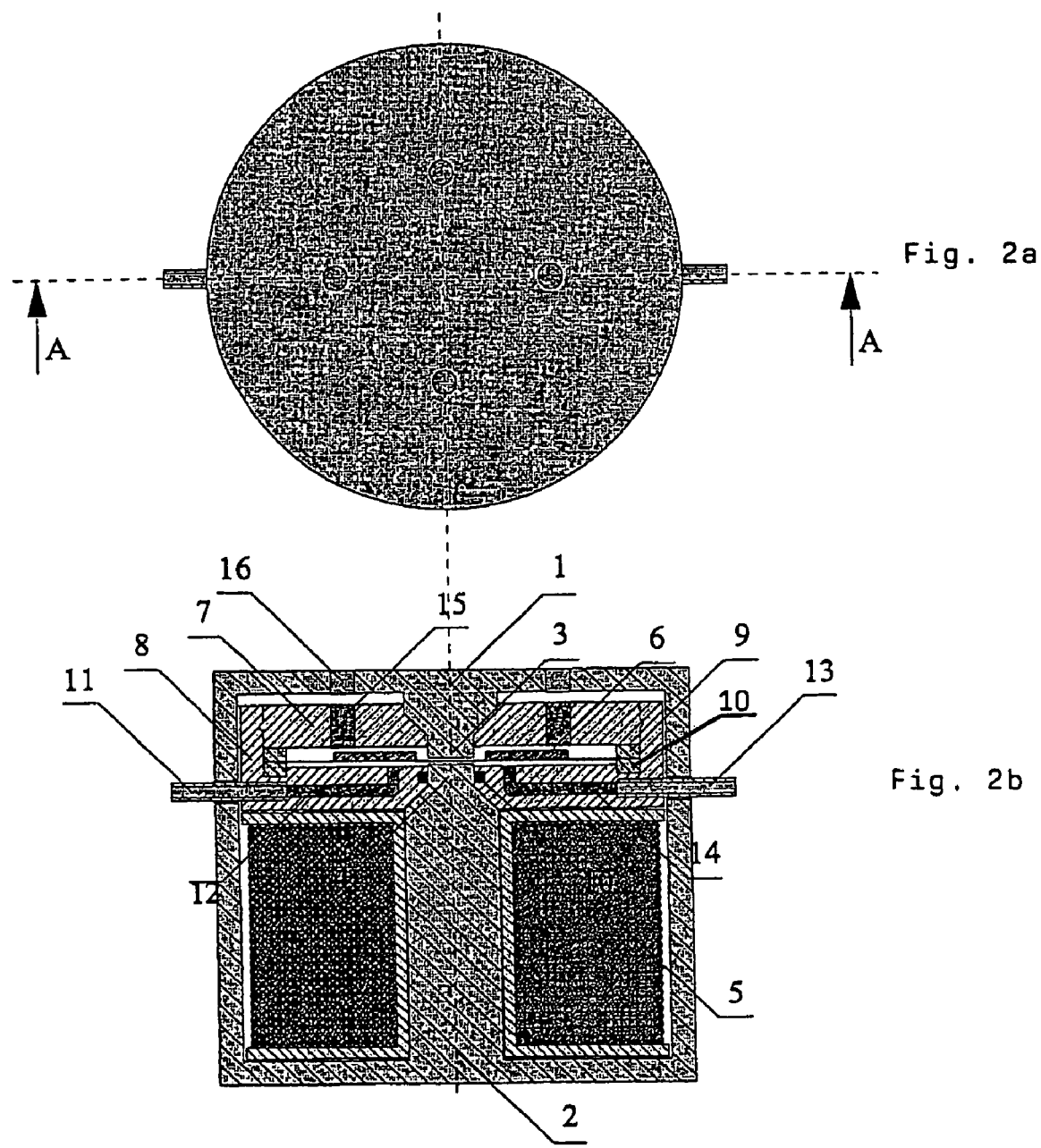

FIG. 2 shows an embodiment of the oxygen sensing apparatus, which has a thin, disk shaped piezoelectric pressure sensor mounted inside the air gap of an electromagnetic circuit. The electromagnetic circuit has a pot core type body, which divides into upper half 1 and lower half 2. The core is preferably constructed of laminated metal sheets to achieve a strong magnetic field, but iron powders and ferrites may be appropriate as well, when higher frequencies are used. The air gap is formed between two opposite surfaces of upper half center tap 3 and lower half center tap 4. The width of the air gap is approximately 200 µm. The pot core also encloses coil 5, which is used to produce magnetic flux into the electromagnetic circuit. The coil is wound around the center tap of lower half of the pot core.

The pressure-sensor 6, which is located in the middle of the air gap, divides the air gap into two different sides in a planar direction. Both sides form airtight chambers as the pressure sensor is enclosed inside a plastic housing, which divides into cover 7 and body 8. The housing has gaskets 9 and 10, made of silicon plastic or rubber, which seal up the joints between the pressure sensors and the pot core taps. The lower chamber, in FIG. 2, has an inlet 11 to conduct a respiratory gas mixture through cavity 12 to between the lower surface of pressure sensor and the upper surface of lower pot core tap. The lower chamber also has an outlet 13, to which a gas pump is connected. The outlet is connected to the lower chamber through a cavity 14. The pump is used to create an underpressure to the outlet, which causes a gas flow through the chamber from the inlet to the outlet. The gas inlet and outlet, as well as electrical connections for the coil and pressure sensor are brought out from the oxygen sensing apparatus through the junction point of the upper and lower halves of the pot core.

The upper chamber has cavities 15 connected to ambient atmospheric pressure through cavities 16 in upper half 1 of the pot core to maintain a constant pressure inside the chamber. No gas flow is needed for the reference side. The pressure sensor is insensitive for constant pressures and a constant underpressure on the sample side produced by the pump cause a zero voltage at the sensor output. However, a sinusoidal pressure ripple caused by the pumping action of the pump's piston, can still be seen as a corresponding sinusoidal voltage at the sensor output. The frequency of this disturbance can be filtered out from the output signal since it is much lower compared to switching frequency 0.5–5 kHz of the pulsating magnetic field.

Figure 3A:
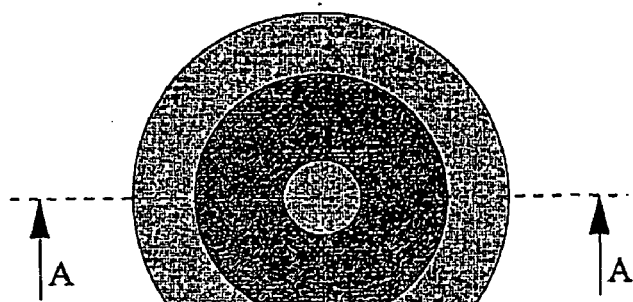
FIGS. 3a and 3b are a top view and cross-sectional view, respectively of one embodiment of a pressure sensor incorporated in the paramagnetic oxygen sensing apparatus of the present invention.
Figure 3B:
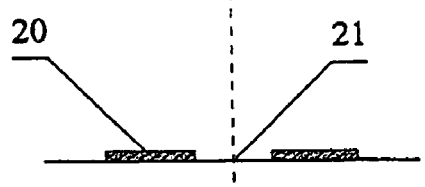

FIG. 3b shows a cross sectional view of an embodiment for the pressure sensor 6. The sensor is constructed of a ring shaped piezoelectric crystal 20, which is attached on the top of a circular membrane 21. The attachment is electrically conductive and is done by gluing, soldering or other similar technique. The piezoelectric element can be one layer or a multilayer bi-morph. The thickness of the piezoelectric element is between 25–500 µm, outer diameter between 10–20 mm, and inner diameter between 2–4 mm. The circular membrane is preferably made of a nonmagnetic material such as BeCu or spring steel, but other materials may fit as well. The thickness of the membrane is between 5–50 µm and diameter between 10–20 mm. The membrane is electrically connected to a lower electrode of the piezoelectric crystal and functions as a ground electrode for the crystal. An electric wire is soldered to another electrode, on the upper surface of the piezoelectric crystal and is connected to measuring electronics. Pressure applied to the membrane side of the sensor structure bows the membrane, which then bends the piezoelectric crystal. This bending causes the electrical properties of piezoelectric crystal to change and a voltage to appear between the electrodes of the piezoelectric crystal. This type of passive sensor can sense very low pressures between 0–5 Pa with the accuracy error of less than 5 mPa. The thin construction of the sensor also enables it to be placed into the narrow cavity between the pot core taps of the electromagnetic circuit.

Figure 4A:
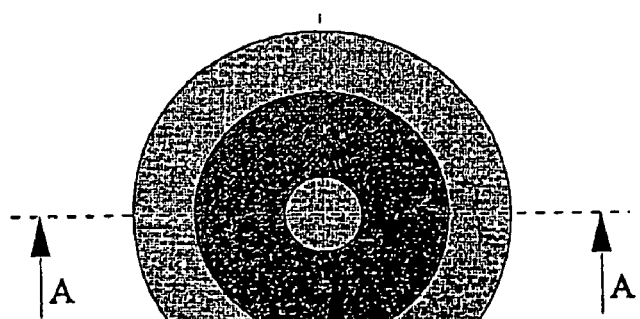
FIGS. 4a and 4b are a top view and cross-sectional view, respectively, of another embodiment of a pressure sensor for the paramagnetic oxygen sensing apparatus.
Figure 4B:
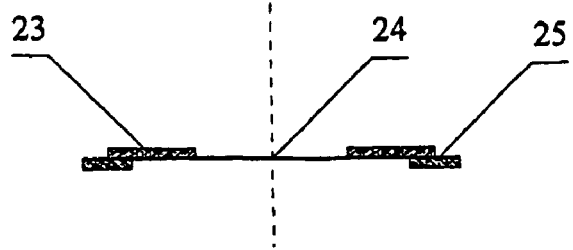

FIG. 4b shows a cross sectional view of another embodiment for the pressure sensor element. The sensor is constructed of a ring shaped piezoelectric crystal 23 attached to the junction point of a circular membrane 24 and a ring shaped supporting structure 25. The attachment is electrically conductive and is done by gluing, soldering or other similar technique. The piezoelectric element can be one layer or a multilayer bi-morph. The thickness of the piezoelectric element is between 25–500 µm, outer diameter between 10–20 mm, and inner diameter between 2–4 mm. The circular membrane is preferably made of nonmagnetic material, such as BeCu or spring steel, but other materials may fit as well. The thickness of the membrane is between 5–50 µm and diameter between 10–20 mm. The ring shaped supporting structure is preferably made of metal. The thickness of the structure is between 100–1000 µm, outer diameter between 10–20 mm, and inner diameter between 10–18 mm. Membrane 24 is electrically connected to a lower electrode of piezoelectric crystal 23 and upper surface of supporting structure 25. The supporting structure thus functions as a ground electrode of the crystal through the membrane. An electric wire is soldered to another electrode, on the upper surface of piezoelectric crystal 23 and is connected to measuring electronics. Pressure applied to the membrane side of the sensor structure bows the membrane and causes a twisting force at the hinge point of the membrane and supporting structure. This twisting is transferred to the piezoelectric crystal, which causes the electrical properties of the piezoelectric crystal to change and a voltage to appear between the electrodes of the piezoelectric crystal.

Figure 5:
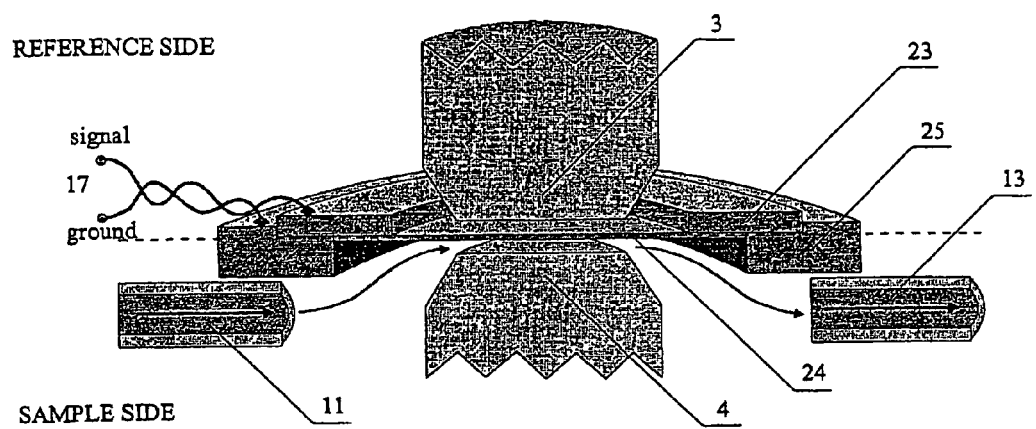
FIGS. 5 and 6 are cross-sectional views of a portion of the paramagnetic oxygen sensing apparatus of FIG. 2 illustrating the operation of the pressure sensor.
Figure 6:
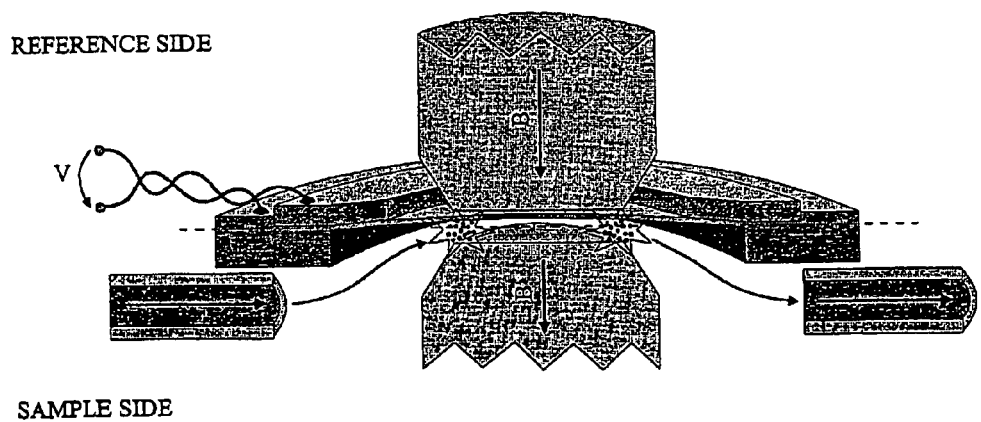

The functioning of the pressure sensor is shown in the cross-sectional of views in FIGS. 5 and 6. A gas pump connected to gas outlet 13 creates a gas flow, of for example breathing gases, through the lower chamber of the housing from inlet 11 to outlet 13. The underpressure created by the pump bows the pressure sensor slightly downwards, but the voltage output 17 of the pressure sensor is zero, since the piezoelectric element is insensitive for constant pressure directed to it. In addition to the pressure sensor bowing, it also vibrates a little in the phase of the sinusoidal piston action of the pump. The frequency of this disturbance is less than 100 Hz, normally around 50–60 Hz, which can be seen as a corresponding sinusoidal voltage at the output 17. Although the underpressure inside the lower chamber does not have much effect on the output voltage of the pressure sensor it should be minimized to prevent the sensor membrane from touching the center tap of the pot core. Minimization can be done with pneumatic designing by keeping the pressure difference between the gas inlet and outlet as small as possible. The sinusoidal pressure ripple caused by the pump is minimized with pneumatic filtering. Furthermore the voltage signal from the sensor output is electrically filtered with band pass filtering, since the pump frequency is much lower than the frequency of output signal.

Now, when the magnetic field is switched on and off cyclically, an alternating pressure signal proportional to the content of oxygen in the measured gas is generated. When the switching cycle is at off state, the magnetic field in the air gap is zero as shown in FIG. 5. The pressure difference between the reference gas in the upper chamber and sample gas in the lower chamber is constant and electrical output of the pressure sensor is zero. When the switching cycle of the pulsating magnetic field is at state of high field strength, as shown in FIG. 6, oxygen molecules in the reference and sample gas move from outside the air gap towards the gradient of the magnetic field appearing near the edges around the air gap. When the partial pressures of oxygen are equal on the reference and sample sides, the pressure difference created during the on state of the magnetic field is zero. This is the case when the partial pressure of oxygen on the sample side equals that of ambient air, that is approximately 21% at 101.325 kPa. As the partial pressure of oxygen increases on the sample side, while the partial pressure of oxygen stays constant on the reference side, the pressure sensor bows during the on state of the pulsating magnetic field, as shown in FIG. 6. The voltage appearing at the electrodes of pressure sensor 6 is proportional to the amplitude of the bowing, and thus to the pressure difference between the reference side and the sample side. The frequency of the pressure signal corresponds to the switching frequency of the pulsating magnetic field, which may be between 0–100 kHz, but preferably 0.1–5 kHz. The maximum pressure difference between 100% oxygen on the sample side and 21% on the reference side can be calculated from the equation below to be approximately 3 Pa, with the magnetic field strength B=2.4 T and temperature T=318.15 K.

The force acting on a molecule in a magnetic field is equal to the magnetic susceptibility of the molecule multiplied by the product of the magnetic field strength and its gradient. In a constant magnetic field the gradient is zero. The molecule can experience a force only in areas where the magnetic field is gradually changing. In a practical magnetic circuit, a constant magnetic field exists inside an air gap between the magnet poles. Outside the gap, the field is rapidly falling to zero. The pressure difference is thus generated between the gas inside and outside the magnetic field. The pressure difference $\Delta p$ between the high magnetic field area and zero field area is proportional to the partial pressure of oxygen $pO_2$ in a gas mixture:

$$\Delta p = \left(\frac{C_m}{2 \cdot \mu_0 \cdot R}\right) \cdot pO_2 \left(\frac{B}{T}\right)^2, \text{ where} \quad (1)$$

$C_m = 1.36 \cdot 10^{-5}$ K/mol is Curie constant per mol
$\mu_0 = 4 \cdot 10^{-7}$ Vs/Am is vacuum permeability
$R = 8.3144$ J/Kmol is gas constant
$B[T]$ is magnetic field strength
$T[K]$ is temperature As the frequency for measuring the oxygen content is fixed to a certain pre-determined value and as most of the disturbances are found from certain bandwidths, it is possible to do some pressure signal pre-filtering already at the pressure sensor. When the piezoelectric element is attached to another mechanical element, for example membrane 21 as shown in FIG. 3, to form a pressure sensor, the attachment affects the mechanical resonance frequency of the piezoelectric element. The attached element functions as the mechanical load to the piezoelectric element. The attached mechanical element will not necessarily vibrate at the same frequencies as the piezoelectric element so that the overall composite sensor construction may have a plurality of mechanically resonant frequencies and a plurality of anti-resonant frequencies. The output signal of the pressure sensor is much weaker at anti-resonant frequencies than at resonant frequencies. The frequencies of mechanical resonance of a piezoelectric element is established by the external dimensions of the element and/or the composition of the piezoelectric material forming the element and can be changed by changing these aspects of the element. This means that the pressure sensor can be so formed as to be mechanically "tuned" to a local resonant frequency, corresponding the frequency of oxygen content measurement, to get a higher output signal at that bandwidth, but a lower output outside of that bandwidth.

The foregoing description describes operation of the paramagnetic oxygen sensing apparatus in a "passive" mode. The following description describes operation of the sensing apparatus in an "active" mode.

When the pressure sensor is used actively, it is excited to vibration near or at the mechanical resonant frequency of the sensor by applying an alternating electrical voltage to its electrodes. An external force, such as the pressure inside the lower chamber, directed to the vibrating sensor functions as a mechanical load for the piezoelectric crystal element and can be measured as a change in electrical properties of the element. Active sensing consumes energy, but it is more sensitive than passive sensing. The sensitiveness depends on the Q-value of the sensor, which determines the sharpness and the amplitude of the resonant frequency spike. On the other hand, the bandwidth of the sensor becomes narrower as the sensitiveness is increased. The main difference between active and passive sensing is that the pressure sensor can also sense static pressures in active sensing. This means that the sensor is sensitive to slow pressure changes such as pressure changes in breathing circuit or static underpressure of the pump. These errors can be minimized with pneumatic circuit design and signal filtering.

The pressure sensor shown in FIG. 2 is also suitable for the use in active sensing on a condition that static pressures are minimized with pneumatic design to such level that the signal detection stays in a linear detection region.

Piezoelectric element 20 of FIGS. 2, 3, and 4 can be used to electrically measure the mechanical strains in the piezoelectric element caused by the external forces applied to the element. These pressures result from differential gas pressures between the chambers acting on membrane 21 in the manner described above in connection with FIGS. 5 and 6. The effects of these mechanical-electrical conversions are most pronounced when they occur along the poling axis of the piezoelectric element established during manufacture and piezoelectric element is formed and mounted to plate 21 such that this will occur. The poling axis will be generally parallel to the plane of a ring-like piezoelectric element 20.

When a mechanical force or electrical energization is applied to a piezoelectric element that does not thereafter change or changes only very slowly, the conversion occurring in the piezoelectric element is somewhat ineffective. For example, the dimensional change in a piezoelectric element resulting from the application of a DC electrical energization is usually measured in nanometers. The conversion from mechanical energy to electrical energy is somewhat more effective and becomes more effective if the mechanical force is rapidly applied. For example, delivering a sharp blow to a piezoelectric element results in an output voltage spike.

When electrical energization that alternates in polarity is applied to a piezoelectric element, the piezoelectric element undergoes mechanical vibration at a frequency corresponding to that of the alternating electrical energization. A piezoelectric element, like other the mechanical objects and structures, will have a natural frequency of vibration. When vibrating at the natural frequency, physical displacements in an object are at maximum amplitude. When the frequency of the alternating electrical energization is that of the natural frequency of the piezoelectric element, the condition is one of mechanical resonance. When converting electrical energy into mechanical energy at the frequency of mechanical resonance of the piezoelectric element, the maximum amplitude of mechanical displacement induced in the piezoelectric element by the alternating electrical energization is much greater, for example, 10–100 times greater, than the maximum displacement that can be obtained from the application of electrical energization that does not change or changes very slowly after application.

Figure 7A:
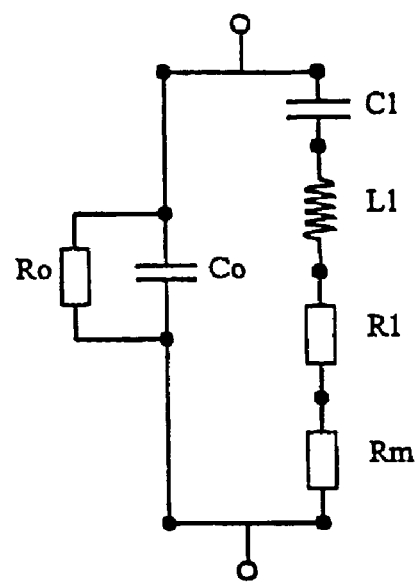
FIG. 7a is an equivalent electrical circuit diagram of a pressure sensor incorporating a piezoelectric element.

To consider the conversion of mechanical energy to electrical energy when a piezoelectric element is driven at the frequency of mechanical resonance, the simple equivalent circuit shown in FIG. 7a may illustrate the electrical characteristics of the piezoelectric element. In the equivalent circuit, capacitance Co is the capacitance of the piezoelectric element and resistance Ro is the dielectric loss of the piezoelectric element. Resistor R1 represents the mechanical loss in the piezoelectric element and resistance Rm represents the mechanical load on the sensor, such as that imposed by membrane 21. Capacitor C1 and inductor L1 represent the rigidity and mass of the material of the piezoelectric element, respectively.

The series and parallel connections of the capacitive and inductive components in the equivalent circuit shown in FIG. 7a cause the overall circuit impedance characteristics to vary with frequency. When a piezoelectric element is vibrated at the frequency of mechanical resonance, the impedance of the piezoelectric element is at its lowest value. The inverse expression of impedance is "admittance," which quantity is used herein for ease of explanation. The admittance of piezoelectric element will be at its greatest value at the frequency of mechanical resonance of the piezoelectric element. Conditions at this frequency resemble the characteristics of a series connected, inductive-capacitance alternating current circuit and are sometimes called that of electrical "resonance."

In addition to the high admittance characteristics appearing at the frequency of mechanical resonance, there will also be a vibration frequency at which the admittance of the piezoelectric element will be at a minimum value. Conditions at this frequency resemble those of a parallel inductive-capacitance alternating current circuit and this point is sometimes called that of "anti-resonance."

Figure 7B:
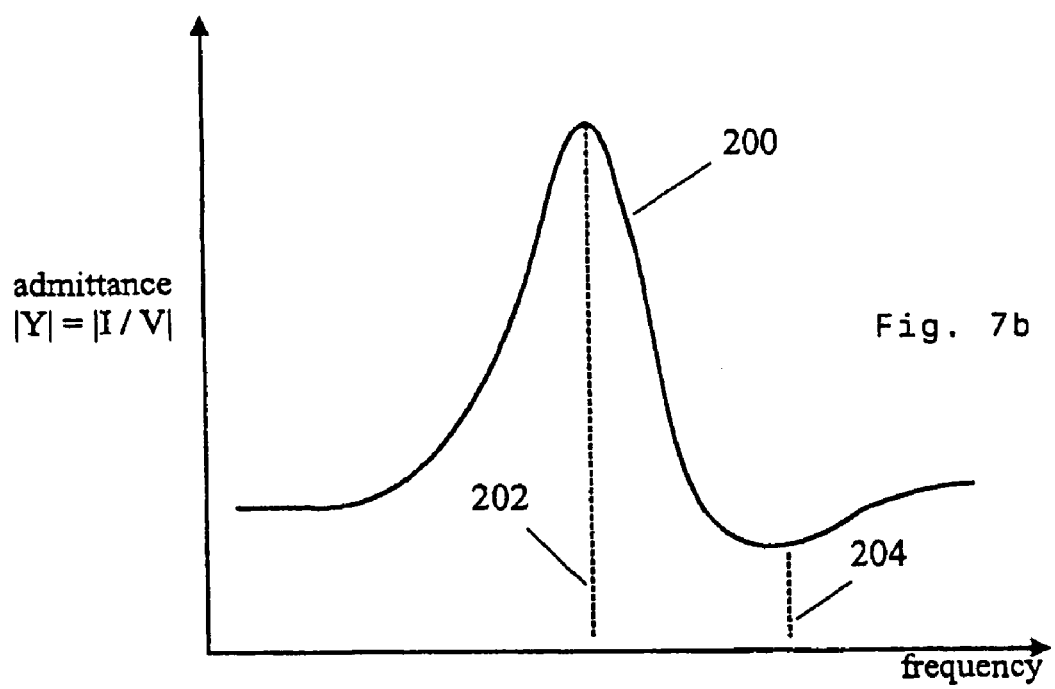
FIG. 7b graphically illustrates a resonance curve of a piezoelectric element.

In FIG. 7b, the ordinate is scaled in the electrical admittance Y of the piezoelectric element. The abscissa is scaled in the frequency. The graph 200 of FIG. 7b shows the electrical admittance Y of a piezoelectric element with respect to the mechanical resonance frequency of the piezoelectric element. The frequency 202 at which the admittance Y is at a maximum value is the mechanical resonance frequency of the element. The minimum value of admittance Y is found at frequency 204, which is characterized as the anti-resonance frequency.

As noted above, the frequency of mechanical resonance of a piezoelectric element is established by the external dimensions of the element and/or the composition of the piezoelectric material forming the element and can be changed by changing these aspects of the element.

When the piezoelectric element is attached to another mechanical element, for example, membrane 21, as shown in FIG. 3, to form a pressure sensor, the attachment affects the mechanical resonance frequency of the piezoelectric element. The attached element functions as the mechanical load to the piezoelectric element. The attached mechanical element will not necessarily vibrate at the same frequencies as the piezoelectric element, so that the overall composite sensor construction may have a plurality of mechanically resonant frequencies, at which the admittance Y is at high values, and a plurality of anti-resonant frequencies, at which the admittance has low values.

Figure 7C:
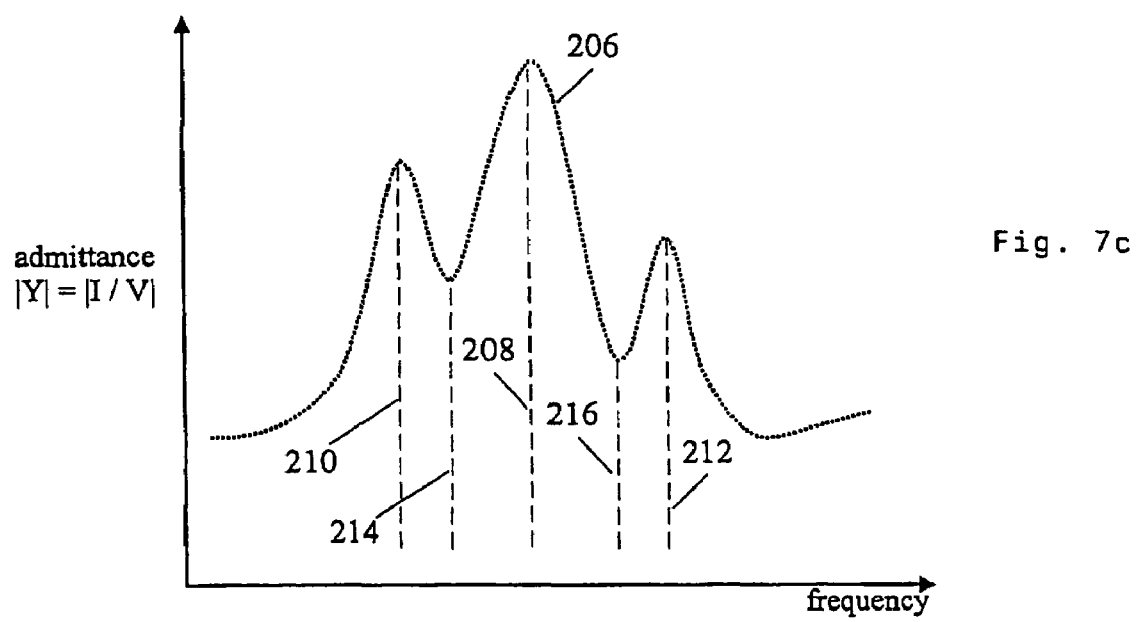
FIG. 7c graphically illustrates a resonance curve for a sensor incorporating a piezoelectric element.

FIG. 7c shows, in a manner similar to FIG. 7b, a graph 206 of admittance Y versus frequency for a composite structure, such as that described above. Vibration of the composite structure at frequencies 208, 210 and 212 produce high values of admittance. Vibration at frequencies 214 and 216 produce low values for admittance Y.

As generally indicated in FIGS. 7b and 7c, the admittance Y values at the peaks of the resonance frequencies are from several to 1000 times higher than those values found in the lower portions of the graph. The width of the peaking portions of the admittance-frequency graphs, in terms of frequency at −3 dB admittance level, is usually from tens of hertz to several kilohertz, depending on the structure of the piezoelectric element and/or composite structure.

Figure 8A:
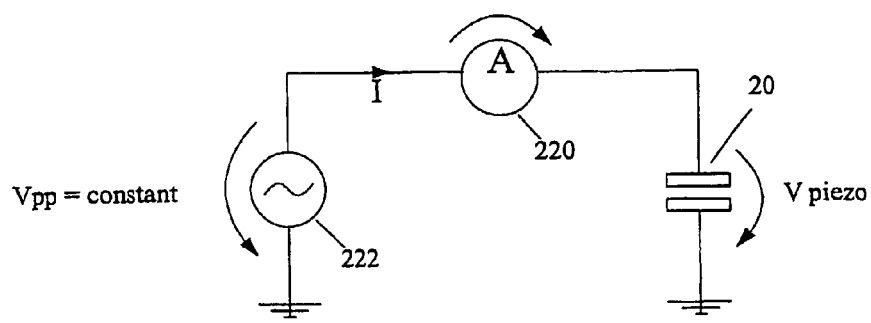
FIGS. 8a, 8b, and 8c are schematic diagrams showing three different techniques for measuring the electrical properties of a piezoelectric element to produce data of the type shown in FIGS. 7b and 7c.

The graphs shown in FIG. 7 may be obtained by measuring the current through a piezoelectric element against the frequency of the electrical signal applied to the piezoelectric element when an alternating electrical energization of constant peak voltage magnitude is applied to the piezoelectric element. The measured current is used to compute the admittance of the piezoelectric element. The frequency that produces the highest current, and hence highest admittance, is the mechanical resonance frequency of the element. FIG. 8a shows circuit that may be used to determine the admittance of a composite construction containing a piezoelectric element. Piezoelectric element 20 is connected in series with ammeter 220 across constant peak voltage magnitude, variable frequency AC voltage source 222. As the frequency of voltage source 222 is varied, the current through piezoelectric element 20 is measured and the admittance determined as Y=I/V.

Figure 8B:
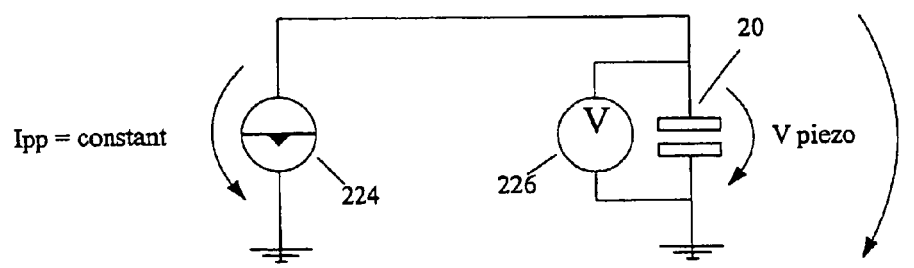

Or a current that alternates between fixed magnitudes may be applied to the piezoelectric element as shown in FIG. 8b. The current source 224 is of adjustable frequency. The voltage across the piezoelectric element is measured by voltmeter 226 as the frequency of the applied current is varied. With the current magnitude so fixed, the voltage across the piezoelectric element will decrease as the admittance of the piezoelectric element increases at the frequency of mechanical resonance. The same formula, Y=I/V, is used to determine admittance.

Figure 8C:
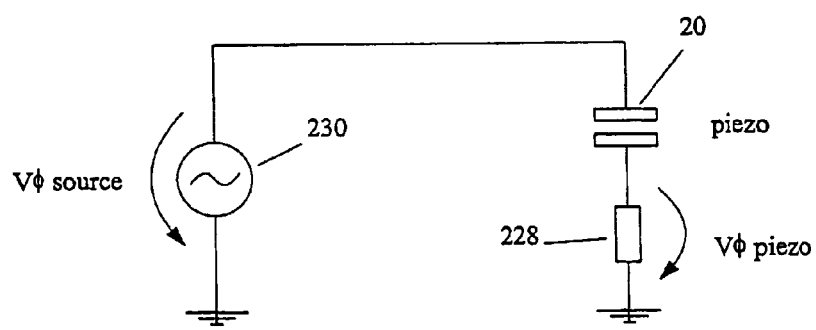

A third way to establish the data shown in FIG. 7 is to measure electrical phase differences occurring in the circuit containing piezoelectric element 20. At the frequency of mechanical resonance, there will be a minimum phase difference, or no phase difference, between the voltage and current in the circuit. See FIG. 8c in which the phase difference may be determined by voltage and load current measurements carried out in connection with resistor 228 and voltage source 230.

An external compressive or tensile load applied to the vibrating piezoelectric structure, as when membrane 21 is subjected to over pressure in the lower chamber, shifts the series resonance frequency or frequencies, such as 202, 208, 210 and 212, and the parallel or anti-resonant frequency or frequencies, such as 204, 214, and 216. The shift in resonance and anti-resonance frequencies will be related to the magnitude of the applied load. Furthermore, the shift in resonance and anti-resonance frequencies for a given applied load is greater when the effect of external force is directed along the poling axis of the piezoelectric element. The characteristics described above are used to measure differential pressures of oxygen content in a breathing gas between the upper and the lower chambers of the pressure sensor in presence of pulsating magnetic field in the following manner.

Figure 9A:
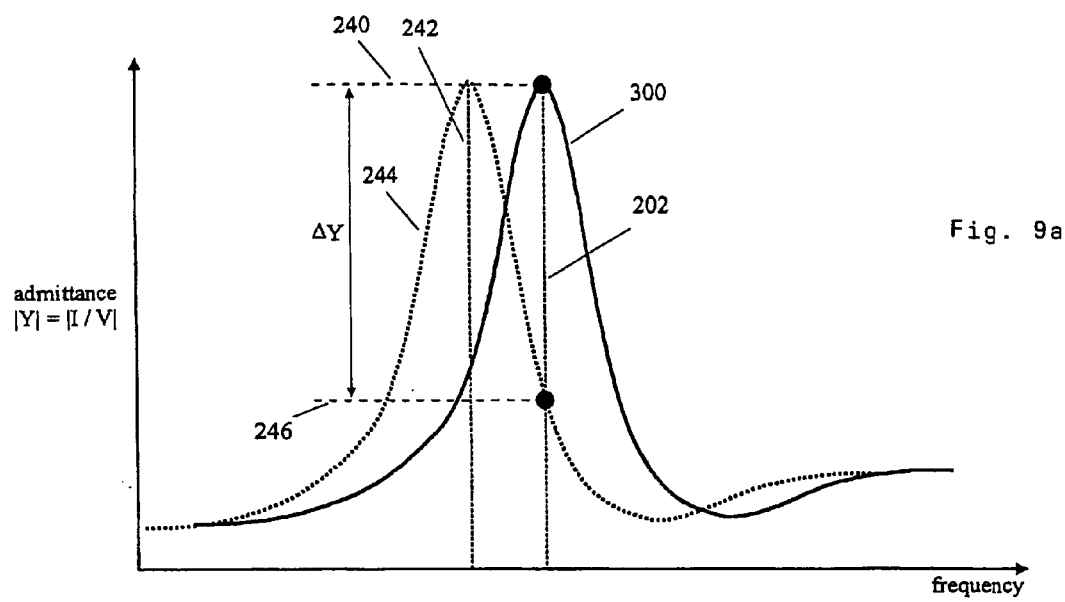
FIGS. 9a, 9b, and 9c are graphs illustrating electrical properties of the pressure sensor of FIG. 7a that can be used to measure the differential pressures in the paramagnetic oxygen sensing apparatus.

For explanatory purposes, FIG. 9a shows a simple admittance-frequency curve 300, similar to that shown in FIG. 7b. It will be appreciated that the actual admittance-frequency curve for a sensor will more generally resemble that of FIG. 7c since piezoelectric element 20 is coupled to membrane 21 to form a composite pressure sensor structure. Piezoelectric element 20 is energized at resonance frequency 202.

As shown in connection with FIGS. 5 and 6, pressure will be applied to membrane 21 of pressure sensor 6 by the partial pressure difference of oxygen between the two chambers. These pressures will, in turn, be applied to piezoelectric element 20. The mechanical loading applied to piezoelectric element 20 will cause the resonance frequency of the piezoelectric pressure sensor structure to shift from frequency 202 to frequency 242, as shown on in FIG. 9a by graph 244. The direction of the shift will depend on the construction of the piezoelectric pressure sensor structure and on whether the mechanical load applied to piezoelectric element 20 is tensile or compressive. With the resonance frequency curve shifted to that shown by graph 244, the admittance Y of the pressure sensor structure measured at the energization frequency 202 will fall to the level 246. The difference in admittance between level 240 and level 246 is a measure of the differential gas pressure between the two chambers. The peaking nature of the graph shown in FIG. 4a at the resonance frequency is useful in providing difference values of a magnitude that assists in accurately determining pressures.

Figure 9B:
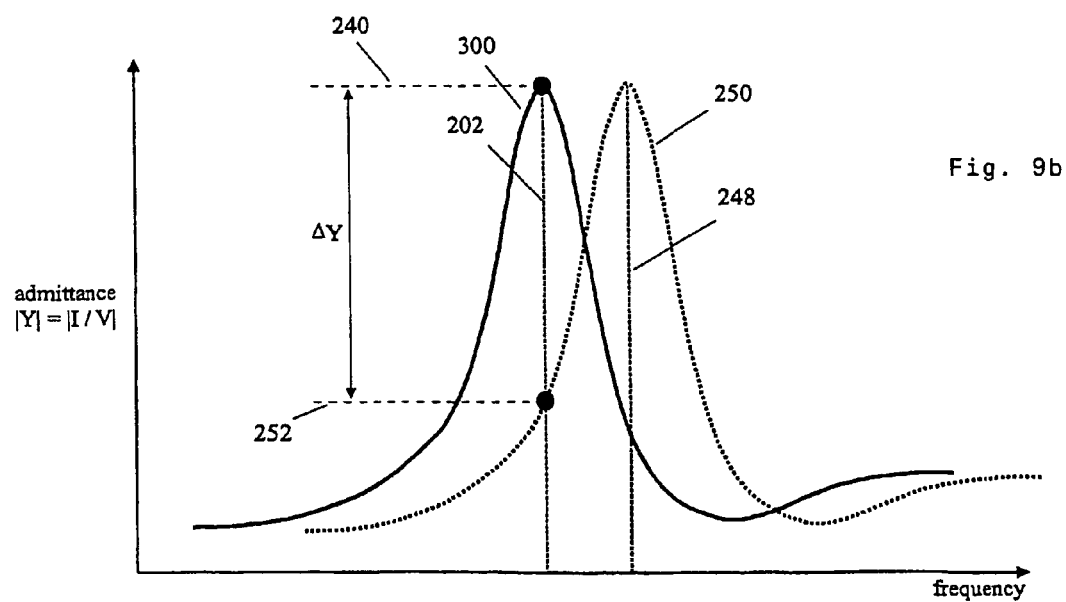

FIG. 9b shows the situation in which the pressure applied to membrane 21 by the gases in the two chambers results in a loading of piezoelectric element 20 that causes the resonance frequency to increase, as shown in the figure by frequency 248 and curve 250. The admittance value Y measured at frequency 202 falls to a level 252 lower than level 240 that may be used to determine partial pressure of oxygen in breathing gas.

While FIGS. 9a and 9b have described operation of pressure sensor using resonance frequency 202, it will be appreciated that the differential gas pressure measuring technique described above will also work should pressure sensor be operated at a frequency other than the resonance frequency. The difference in admittance Y values between the unloaded and loaded states of the piezoelectric sensor structure will tend to be less than those obtained through the use of the resonance frequency 202 and shown in FIGS. 9a and 9b.

Figure 9C:
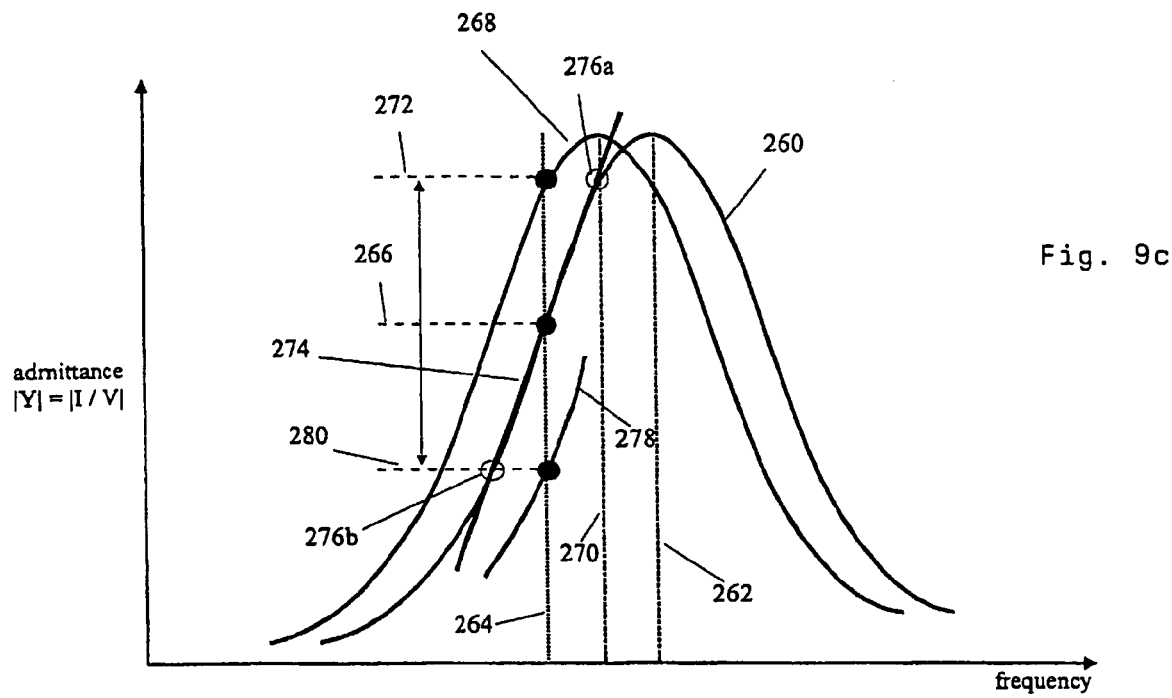

This technique to measure gas pressure magnitude is shown in FIG. 9c. In this technique, the characteristics of admittance versus frequency, shown graphically in FIG. 9c as curve 260, are determined for a state in which the piezoelectric pressure sensor structure is not subject to any mechanical loading. The graph will exhibit a resonance frequency 262.

Pressure sensor 6 is then operated to supply electrical energization to piezoelectric element 20 at a frequency 264, different from frequency 262 and the admittance Y of the unloaded state is measured, as level 266 which value is used as a reference signal.

Thereafter, the piezoelectric pressure sensor structure is subjected to the differential pressure caused by the gases oxygen content difference between the two chambers in presence of a pulsating magnetic field. The mechanical loading applied to piezoelectric element 20 by the differential pressure will shift the admittance-frequency curve, as shown in FIG. 9c by graph 268. This shift will cause the admittance of the piezoelectric pressure sensor structure measured at frequency 264 to change to the value indicated by level 272. The change in admittance value can be used to determine the oxygen content of the breathing gas.

The frequency 264 used for measuring purposes can be chosen in accordance with the construction of the piezoelectric pressure sensor structure and the minimum and maximum differential pressures to be measured. It is usually spaced tens or hundreds of hertz greater or lower than the resonance frequency 262. Also, it is desirable to select a frequency 264 that lies in a generally linear portion of graph 260 for the range of differential pressures to be measured. This provides linearity in the measurement of differential pressure within the pressure range. A linear portion of curve 260 is shown by line 274 and dots 276a and 276b.

When the mechanical loading applied to piezoelectric element 20 by the differential pressure on membrane 21 is opposite to that described above, the admittance versus frequency curve will shift in the opposite direction from that described above. This is shown by the partial curve 278 in FIG. 9c. In this circumstance, the admittance value Y measured at frequency 264 will decrease to level 280. The difference between the admittance value 266 and the admittance value 280 may be used to determine the oxygen content of the breathing gas. The fact that the admittance value 280 is decreased from admittance value 266 indicates that the loading on piezoelectric element 20 is opposite that which produces admittance level 272.

While FIG. 9c shows operation of pressure sensor at a frequency 264 less than resonance frequency 262, it will be appreciated that pressure sensor may be operated in an analogous manner for a frequency greater than frequency 262. The changes in admittance caused by a compressive loading of piezoelectric element 20 and a tensile loading of the piezoelectric element will be opposite to that described above in connection with FIG. 9c.

A benefit achieved in measuring the partial pressure of oxygen at a frequency point aside from the natural resonant frequency point is lower power consumption. However, to ensure that the admittance measurements are sufficient to measure pressure changes with the desired degree of accuracy, the amplitude of alternating voltage supplied to the piezoelectric element 20 must be sufficiently high to provide the desired signal to noise the ratio in the signals used for measurement.

Figure 10:
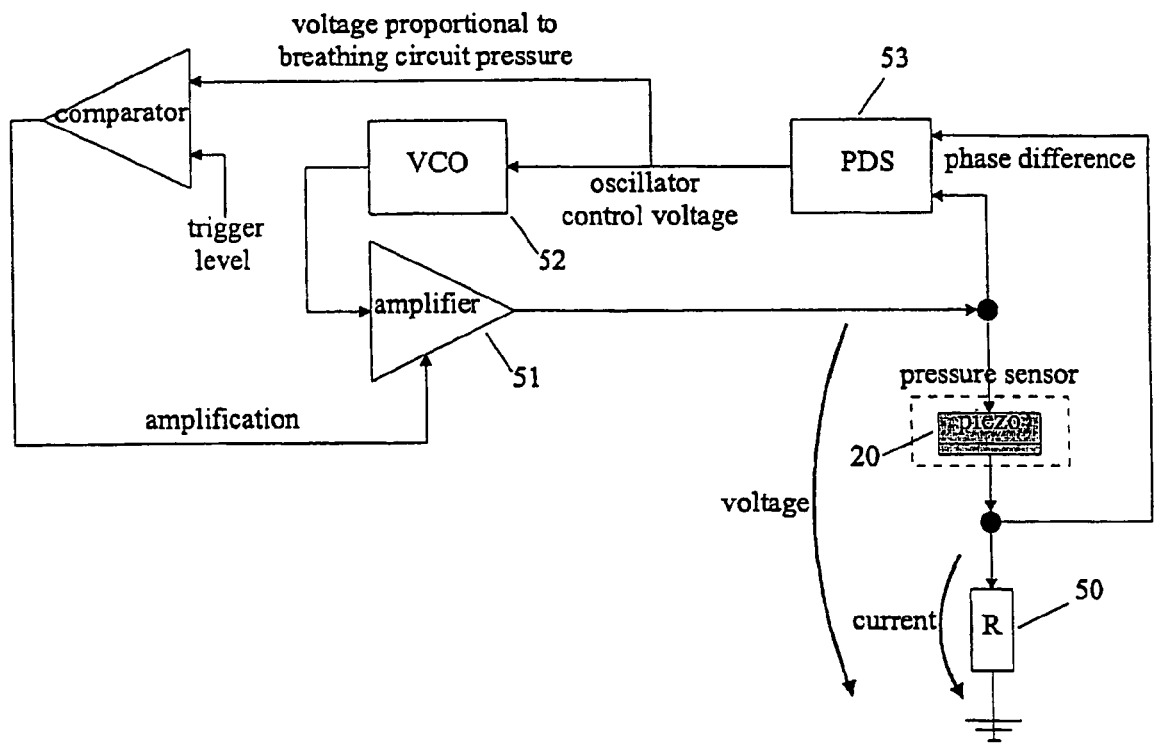
FIG. 10 is a schematic diagram of circuitry for use with a further technique for measuring differential pressures in paramagnetic oxygen sensing apparatus.

A further technique to measure differential pressure magnitude between the two chambers is based on electrical phase differences between the voltage and current in piezoelectric sensor 6 and is shown in FIG. 10. A circuit for measuring phase difference includes resistor 50 in series with piezoelectric element 20. Resistor 50 corresponds to resistor 228 shown in FIG. 8c. The voltage across resistor 50 is an indication of the current through piezoelectric element 20. The output of amplifier 51 containing the amplified output of voltage controlled oscillator 52 is an indication of the voltage applied to piezoelectric element 20. The current signal from resistor 50 and the voltage signal from the amplifier 51 are applied to phase displacement detection system 53 respectively. Phase displacement detection system 53 determines the phase difference between the two signals, as by detecting zero crossings or some other appropriate technique, and provides a phase difference output signal.

At the resonance frequency of the pressure sensor, when there is no mechanical loading on the sensor due to a zero pressure or "normal" conditions inside the two chambers of pressure sensor 6, the phase difference between the current and voltage is zero or close to zero. When a pressure difference occurs between the two chambers, as when the magnetic field is connected on, this shifts the resonance frequency of the pressure sensor, for example, to a lower frequency than the frequency of the output signal of voltage controlled oscillator which is at the resonance frequency of the piezoelectric sensor in the zero gas pressure difference state. These conditions result in a phase difference between the current as reflected in the voltage measured across resistor 50 and the voltage output of amplifier 51. The phase difference may be one in which the phase of the current is behind the phase of the voltage. If the voltage signal is used as a reference, the phase difference may be deemed a "negative" phase difference; i.e. the current lags the voltage.

This "negative" phase difference is detected by phase displacement detection system 53. Phase displacement detection system 53 then controls voltage-controlled oscillator 52 by, for example, decreasing the oscillator control voltage to alter the frequency of the voltage controlled oscillator to minimize the phase difference. As the oscillator control voltage is decreased, the oscillator output frequency also decreases and the phase difference between the current and the voltage decreases. As the magnitude of pressure difference ceases between the chambers, the need to decrease the oscillator control voltage also lessens. Finally, when the differential pressure between the chambers has reached its minimum value, the phase difference again becomes zero, due to the fact that the energization frequency from voltage controlled oscillator 52 has been set to the resonance frequency of the pressure sensor at the minimum pressure difference condition. At this point, the oscillator control voltage from phase displacement detection system 53 is minimum. The change in oscillator control voltage provided by phase displacement detection system 53 is an indication of the partial pressure difference of oxygen between the two chambers of the pressure sensor in presence of a pulsating magnetic field.

As the pressure difference between the two chambers of pressure sensor 6 starts to revert back to its original condition, as the magnetic field is removed, the phase difference between the current and the voltage again increases but in the opposite direction, i.e. a "positive" phase difference. The new resonance frequency point which was established shifts back to the original resonance frequency as the differential pressure returns to the zero pressure or baseline condition. The "positive" phase difference is detected by phase displacement detection system 53, which then increases the oscillator control voltage for voltage controlled oscillator 52 toward its original value to again minimize the phase difference between the current and voltage in pressure sensor 6. As the oscillator control voltage is increased, the oscillator output frequency also increases and the phase difference in pressure sensor 6 decreases. As the differential pressure between the two chambers of pressure sensor 6 reaches its original value, the phase difference becomes minimized, or zeroed, as the oscillator control voltage and oscillator output frequency reach the same values that established the original zero phase difference.

Figure 11A:
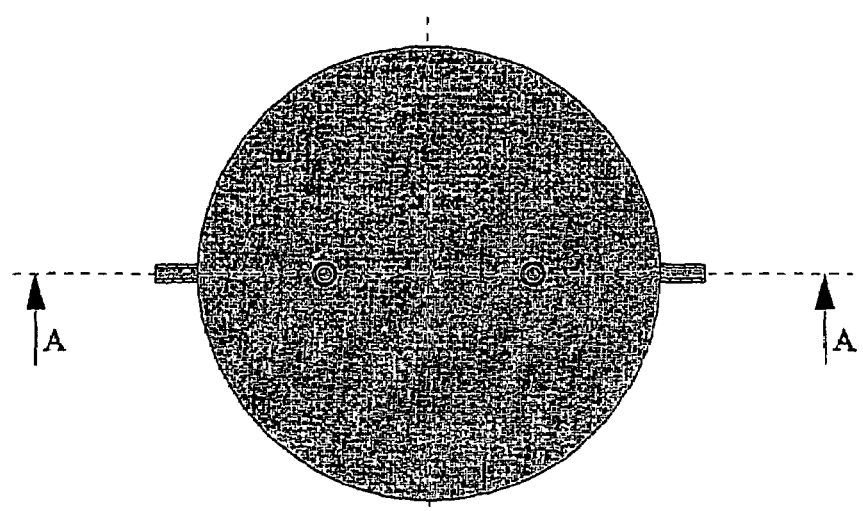
Figure 11B:
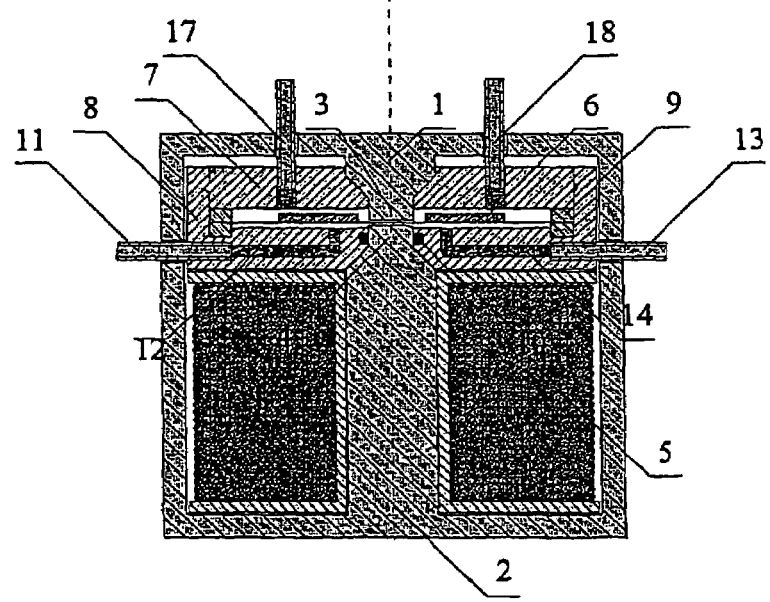

If desired, it is possible to create a reference gas flow through the upper chamber similar to gas flow through the lower chamber. Another embodiment of mechanical construction for the pressure sensor is shown in FIG. 11. The construction in FIG. 11 is identical to that shown in FIG. 2 with a difference that reference gas flow through the upper chamber is similar to gas flow through the lower chamber, which is to minimize static pressure between the two chambers. The reference gas flow is conducted into the upper chamber through reference gas inlet 17 and conducted out through reference gas outlet 18. Reference gas outlet 18 and sample gas outlet 13 are connected through identical pneumatic circuits to a pressure pump. Reference inlet 17 and sample inlet 11 are similarly connected to identical pneumatic circuits with a difference that sample inlet may be connected to a patient breathing circuit. Pressures inside both chambers of the pressure sensor should be equal to keep the sensor signal detection in a linear detection region.

The invention claimed is:

1. A sensing apparatus for measuring the amount of a given gas in a gas mixture, said sensing apparatus utilizing the magnetic susceptibility properties of the given gas and comprising:

a magnetic core having a pair of elements spaced to form an air gap;

means for generating a magnetic field that traverses said air gap;

a deflectable membrane extending through said air gap;

means forming a chamber on each side of said membrane;
means for supplying the gas mixture to one of said chambers, the other of said chambers containing a reference gas; and
a mechanical-electrical conversion element mounted on said membrane and responsive to deflection of said membrane by the gas mixture and reference gas in said chambers when a magnetic field is present in the air gap to provide an indication of the amount of the given gas in the gas mixture.

2. The sensing apparatus according claim 1 wherein said mechanical-electrical conversion element comprises a piezoelectric element.

3. The sensing apparatus according claim 1 wherein said mechanical-electrical conversion element is formed as an annular member mounted on said membrane.

4. The sensing apparatus according to claim 2 wherein said piezoelectric element is mounted on said membrane so that the mechanical-electrical conversion occurring in said piezoelectric element occurs along a poling axis of said piezoelectric element.

5. The sensing apparatus according to claim 1 further including a support for mounting said membrane to said chambers.

6. The sensing apparatus according to claim 1 further including means for providing a flow of the gas mixture through said one of said chambers.

7. The sensing apparatus according to claim 1 wherein said other of said chambers contains ambient air.

8. The sensing apparatus according to claim 6 wherein said other of said chambers contains ambient air.

9. The sensing apparatus according to claim 1 further including means to provide a flow of the reference gas through the other of said chambers.

10. The sensing apparatus according to claim 1 wherein said mechanical-electrical conversion element generates an electrical signal responsive to the deflection of said membrane and wherein a magnitude of said electrical signal provides an indication of the amount of the given gas in the gas mixture.

11. The sensing apparatus according to claim 1 wherein said mechanical-electrical conversion element vibrates mechanically responsive to the application of alternating electrical energization to said element, said element having an admittance, the admittance of said element at a given frequency of alternating electrical energization being alterable by deflection of the membrane, said sensing apparatus further comprising;
means for applying alternating electrical energization to said element; and
admittance measuring means coupled to said element for measuring the admittance exhibited by said element when alternating electrical energization is applied to said element and said membrane is deflected by the gas mixture and reference gas in said chambers to provide an indication of the amount of the given gas in the gas mixture.

12. The sensing apparatus according to claim 11 wherein said admittance measuring means is further defined as measuring the admittance exhibited by said element at a resonant frequency alternating electrical energization.

13. The sensing apparatus according to claim 11 wherein said admittance measuring means is further defined as measuring the admittance exhibited by said element at a frequency other than the resonant frequency of alternating electrical energization.

14. The sensing apparatus according claim 11 wherein said admittance measuring means comprises:
means for applying alternating electrical energization having a desired voltage property which is constant in magnitude to said element;
means for measuring the current through said element; and
means for determining the admittance exhibited by said element from the voltage property and the measured current value.

15. The sensing apparatus according to claim 11 wherein said admittance measuring means comprises:
means for applying alternating electrical energization having a desired current property which is constant in magnitude to said element;
means for measuring the voltage across said element; and
means for determining the admittance exhibited by said element from the current property and the measured voltage.

16. The sensing apparatus according to claim 11 wherein said admittance measuring means comprises means for ascertaining phase shifts occurring in the alternating electrical energization as a result of its application to said element.

17. The sensing apparatus according to claim 1 further defined as a sensing apparatus for measuring the amount of a given gas in a gas mixture by utilizing the positive magnetic susceptibility, paramagnetic properties of the given gas.

18. The sensing apparatus according to claim 17 further defined as a sensing apparatus for measuring the amount of oxygen in a gas mixture.

19. The sensing apparatus according to claim 18 further defined as one for measuring the oxygen content of the breathing gases of a subject.

20. A method for measuring the amount of a given gas in a gas mixture utilizing the magnetic susceptibility properties of the given gas, said method comprising the steps of:
(a) forming an air gap across which a magnetic field can flow;
(b) placing a deflectable membrane through the air gap;
(c) forming a gas chamber on each side of the membrane;
(d) supplying the gas mixture to one of said chambers, the other of said chambers containing a reference gas;
(e) periodically providing a magnetic field across the air gap and through the chambers containing the gas mixture and reference gas, differing responses of the gas mixture and the reference gas to the magnetic field deflecting the membrane; and
(f) sensing the deflection of the membrane as a measurement of the amount of the given gas in the gas mixture.

21. The method according to claim 20 further defined as providing a mechanical-electrical conversion element in operative association with the membrane for sensing the deflection of the membrane and for providing an indication of the amount of the given gas in the gas mixture.

22. The method according to claim 21 further defined as providing a piezoelectric element in operative association with the membrane for sensing the deflection of the membrane.

23. The method according to claim 22 further defined as sensing the deflection of the membrane by mechanical-electrical conversion occurring along a poling axis of the piezoelectric element.

24. The method according to claim 20 wherein the step of supplying the gas mixture to one of the chambers is further defined as flowing the gas mixture through the one of the chambers.

25. The method according to claim 20 wherein the other of the chambers contains ambient air.

26. The method according to claim 24 wherein the other of the chambers contains ambient air.

27. The method of claim 20 further defined as flowing reference gas through the other of the chambers.

28. The method according to claim 20 wherein step (e) is further defined as providing the magnetic field at a switching frequency of up to 100 kHz.

29. The method according to claim 28 wherein step (e) is further defined as providing the magnetic field at a switching frequency of 0.1 to 5 kHz.

30. The method according to claim 21 wherein the mechanical-electrical conversion element generates an electrical signal responsive to the deflection of the membrane, the magnitude of which provides an indication of the amount of the given gas in the gas mixture.

31. The method according to claim 21 wherein the mechanical-electrical conversion element mechanically vibrates responsive to the application of alternating electrical energization to the element, the element having an admittance, the admittance of the element at a given frequency of alternating electrical energization being alterable by a mechanical loading of the element, said method further including the steps of:
   (g) applying alternating electrical energization to the element at a selected frequency;
   (h) measuring the admittance exhibited by the element when subjected to loading by the deflection of the membrane and energized by electrical energization of the selected frequency; and
   (i) using the admittance properties of the mechanical-electrical conversion element as a measurement of the amount of the given gas in the gas mixture.

32. The method according to claim 31 wherein the mechanical-electrical conversion element has a resonance frequency at which the admittance of the element has a peak value and wherein step (g) is further defined as applying alternating electrical energization to the element at the resonance frequency.

33. The method according to claim 31 wherein the mechanical-electrical conversion element has a resonance frequency at which the admittance of the element has a peak value and wherein the step (g) is further defined as applying alternating electrical energization to the element at a frequency other than the resonance frequency.

34. The method according to claim 31 further including a step (j) of measuring the admittance exhibited by the element when the membrane is in an unloaded state when energized by the electrical energization of the selected frequency and wherein the method further includes the step (k) of measuring the difference between the admittances measured in step (h) and (j) as a measurement of the amount of the given gas in the gas mixture.

35. The method according to claim 31 wherein the step of measuring the admittance exhibited by the element further comprises the steps of:
   applying alternating electrical energization having a desired voltage property which is constant in magnitude to the element;
   measuring the current through the element; and
   determining the admittance exhibited by the element from the voltage property and measured current value.

36. The method according to claim 31 wherein the step of measuring the admittance exhibited by the element further comprises the steps of:
   applying alternating electrical energization having a desired current property which is constant in magnitude to the element;
   measuring the voltage across the element; and
   determining the admittance exhibited by the element from the current property and the measured voltage.

37. The method according to claim 31 wherein the step of measuring the admittance exhibited by the element is further defined as ascertaining phase shifts in the alternating electrical energization.

38. The method according to claim 20 further defined as a method for measuring the amount of a given gas in a gas mixture utilizing the positive magnetic susceptibility, paramagnetic properties of the give gas.

39. The method according to claim 20 further defined as a method for measuring the amount of oxygen in a gas mixture.

40. The method according to claim 39 further defined as a method for measuring the oxygen content of the breathing gases of a subject.

* * * * *